United States Patent [19]

Orphan et al.

[11] 4,317,632
[45] Mar. 2, 1982

[54] METHOD AND MEANS FOR OPTICAL INSPECTION OF THE INTERIOR SURFACE OF TUBING

[75] Inventors: Victor J. Orphan, Leucadia; Robert O. Ginaven, Encinitas, both of Calif.

[73] Assignee: Electric Power Research Institute, Inc., Palo Alto, Calif.

[21] Appl. No.: 86,572

[22] Filed: Oct. 19, 1979

[51] Int. Cl.³ ............................................. G01N 21/88
[52] U.S. Cl. .................................................... 356/241
[58] Field of Search ......................................... 356/241

[56] References Cited

U.S. PATENT DOCUMENTS 2,987,960  6/1961  Sheldon .......................... 356/241 X
3,637,314  1/1972  Groot .............................. 356/241 X

FOREIGN PATENT DOCUMENTS

52-21719  2/1977  Japan .................................... 356/241
1372413  10/1974  United Kingdom ................ 356/241

Primary Examiner—John K. Corbin
Assistant Examiner—Matthew W. Koren
Attorney, Agent, or Firm—Flehr, Hohbach, Test, Albritton & Herbert

[57] ABSTRACT

The interior surface of a pipe is optically inspected by a scanner including an array of photodiodes, a light source, and mirrors for directing light reflected from the interior surface to the photodiode array. The charges developed by the photodiodes are converted to digital data which is subtracted from a reference signal for an unblemished interior surface area. The difference is recorded in a memory and displayed on a monitor for defect analysis.

8 Claims, 17 Drawing Figures

ISOMETRIC

FIG.—4A

CONTOUR

FIG.—4B

PROFILE

METHOD AND MEANS FOR OPTICAL INSPECTION OF THE INTERIOR SURFACE OF TUBING

This invention relates generally to optical inspection equipment, and more particularly the invention relates to a method and means for optically inspecting the interior surface of a tube and the like for defects.

The detection of flaws such as dents, cracks, and pits in the interior surface of tubes is particularly important in electrical power generation plants where steam under high pressure is transferred through metal pipes. Heretofore, eddy current testing has been employed to inspect such surfaces. However, tube denting in regions near tubing support plates produces complex eddy current signals which may mask flaws.

Miniature television cameras are available for inspection of surfaces. However, use of a TV camera for inspecting the interior surface of a tube is difficult because of the necessity of rotating either the camera or a mirror assembly in order to view the entire circumference of the tube. Further, a TV camera may not offer long term reliability.

Accordingly, an object of the present invention is an improved method and means for inspecting the interior surface of a tube and the like.

Another object of the invention is optical inspection means which is rugged and reliable.

Another object of the invention is optical inspection means which provides an undistorted image of the tube interior surface.

Still another object of the invention is a method of inspecting the interior surface of a tube and the like with improved dependability.

Another object of the invention is optical inspection apparatus which generates data in a format which is amenable to digital image enhancement and defect quantification.

Yet another object of the invention is optical inspection apparatus which can be used during in-service operation.

Briefly, in accordance with the present invention, means for inspecting the interior surface of a tube and the like includes a light source, means for receiving light and generating an electrical signal in response thereto, and means for directing light onto the means for receiving light. Carrier means is provided for supporting and moving the light, the means for receiving light, and the means for directing light.

More particularly, the means for receiving light and generating an electrical signal preferably comprises an array of photodiodes, and the means for directing light comprises a lens for focusing light onto the array of photodiodes with mirror means provided for reflecting light to the lens.

The carrier means preferably includes an elongated body with a cavity defined therein with the array of photodiodes being mounted within the cavity. A light source is mounted to the carrier to illuminate the interior surface, and the elongated body is provided with an optical window with a convex mirror mounted within the optical window for receiving light reflected from the interior surface. A flat mirror is mounted at one end of the cavity for receiving reflected light from the convex mirror and directing the light to the lens.

By illuminating the interior surface and directing reflected light from the interior surface to the photoelectric means, an electrical signal is generated which is indicative of the intensity of light reflected from the interior surface.

In a preferred embodiment, a reference digital signal is generated for reflected light from an unblemished area of the interior surface, and the electrical signals generated during the inspection process are converted to digital signals with the digital signals subtracted from the stored reference signal. Thus, the signal representing the visual inspection will be near zero for unblemished interior surfaces and increases in response to diminished reflected light due to blemishes on the interior surface.

The invention and objects and features thereof will be more fully understood from the following detailed description and appended claims when taken with the drawing.

Figure 1:
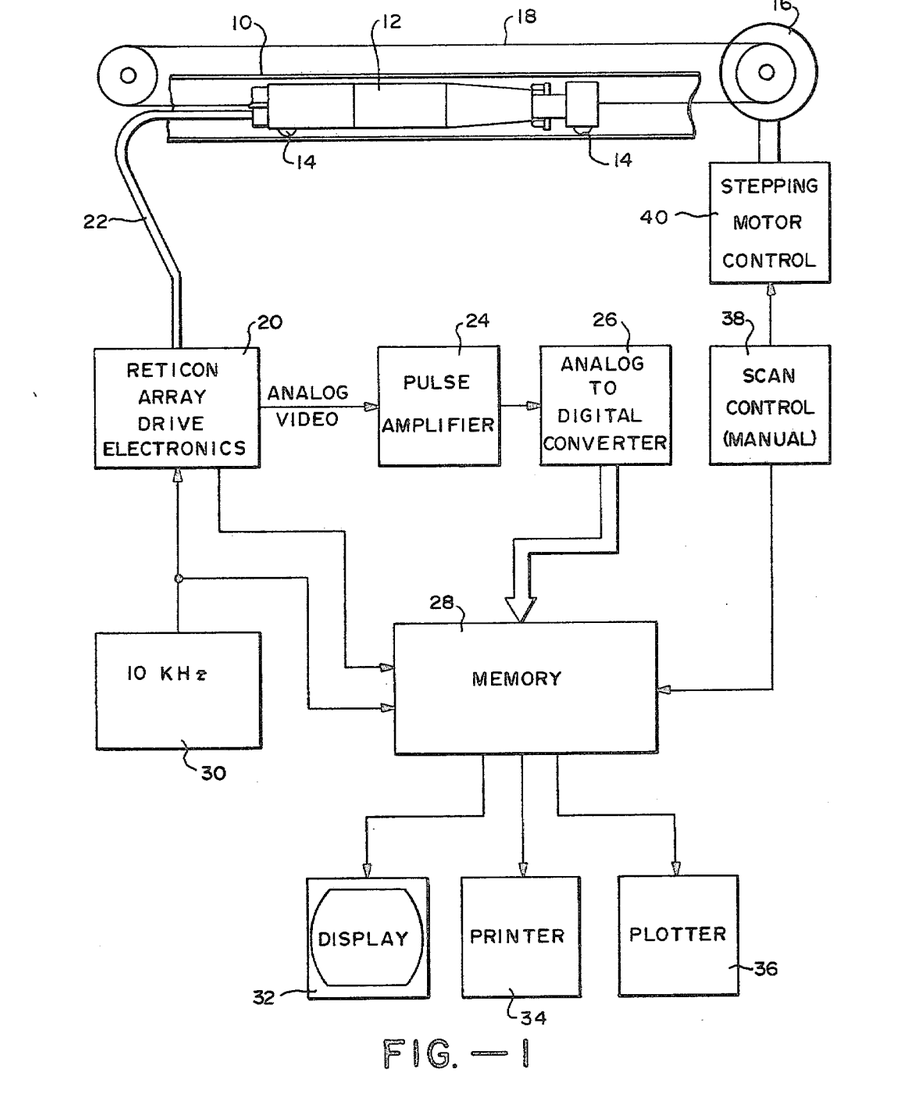
FIG. 1 is a functional block diagram of an optical inspection scanning system in accordance with the present invention.

Referring now to the drawings, FIG. 1 is a functional block diagram of an optical scanner system in accordance with the present invention for inspecting the interior surface of a tube 10. The system includes a carrier 12 having a plurality of wheels 14 which engage the interior surface of tube 10 whereby the carrier can be moved through the length of the tube by means of a stepping motor 16 which drives the carrier 12 by means of cable 18.

As will be described further hereinbelow with reference to FIG. 2, carrier 12 includes a scanner including means for receiving light reflected from the interior surface of pipe 10 and generating an electrical signal. In a preferred embodiment the scanner includes a monolithic array of silicon photodiodes such as the Reticon array, Model RO64, which is a monolithic array of 64 silicon photodiodes uniformly spaced on a 2 millimeter diameter circle. The scanner is connected to drive electronics 20 by means of electrical cable 22. The array is self scanned by an integrated 64 stage ring counter, and the analog signal generated by the photo-diodes is passed to a pulse amplifier 24 and an analog to digital converter 26 with the digital signal stored in a memory 28. As conventionally employed with a Reticon photodiode array, an oscillator 30 provides suitable clock signals for the Reticon array drive electronics and to the memory 28. The stored data in memory 28 can later be analyzed by means of a video display 32, a printer 34, or plotter 36. The rate of scanning may be established manually by scan control 38 which is interconnected with the stepping motor control 40.

Figure 2:
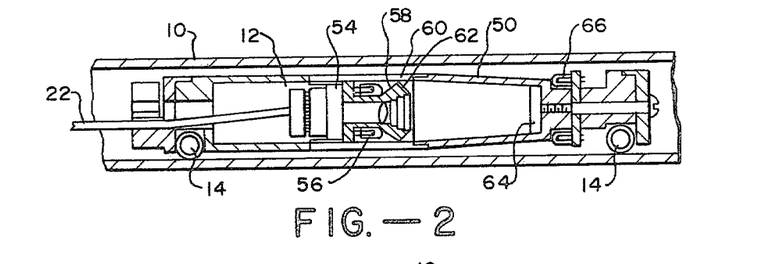
FIG. 2 is a section view of one embodiment of an optical scanner in accordance with the present invention.

Referring to FIG. 2, scanner 12 inside of tube 10 of FIG. 1 is shown in cross section and includes an elongated body 50 with a cavity 52 therein. The photodiode array 54 is mounted within cavity 52 with the electrical outputs from the array connected to cable 22. A plurality of lamps 56 are positioned on a steel mount 58 in close proximity to the diode array for illuminating the interior surface of tube 10 through optical window 60 made of suitable transparent material. An end portion of mount 58 is shaped and polished to provide a spherical convex mirror for directing reflected light from the interior surface to a flat mirror 64 mounted at one end of cavity 52. A second plurality of lamps 66 may be provided for directing light at a grazing angle to the convex lens 62 and thence to the flat mirror 64. Light reflected from the flat mirror 64 is directed to lens 68 which focuses the reflected light on the surface of the photodiode array 54.

Figure 3:
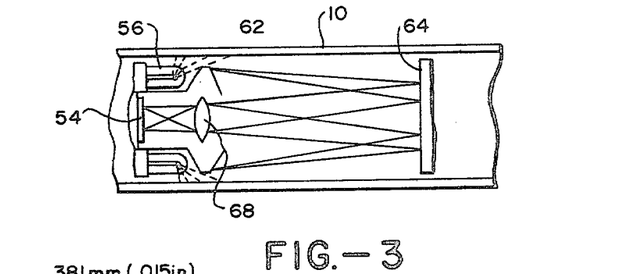
FIG. 3 illustrates the optical path for reflected light in the optical scanner of FIG. 2.

FIG. 3 is a section view of a portion of the scanner of FIG. 2 and further illustrates the path of reflected light from the lamps 56 to the photodiode array 54. As illustrated, light from lamp 56 strikes the interior surface of tube 10 and is reflected off the surface of convex mirror 62. The reflected light then strikes flat mirror 64 and is directed to lens 68. Lens 68 then focuses the reflected light onto the surface of the photodiode array 54.

In one embodiment utilizing the Model RO-64 Reticon array, the interior circumference of an 18 millimeter diameter tube was inspected. The lens utilized was a double convex lens of 5 millimeter aperture and 9 millimeter focal length. The convex mirror was stainless steel which was machined and polished to a spherical surface. The 64 silicon photodiodes of the Reticon array were self-scanned in a clockwise direction by an integrated 64 stage ring counter with the charge generated by each of the diodes being read out sequentially during each scan onto a single output line.

The read out rate is set by the frequency of the complementary square wave clock signals which drive the ring counter, and a sync pulse output is provided once each scan. A Tracor Northern Model NS 623 analog to digital converter and a Tracor Northern Model NS 636 memory were utilized for converting and storing data. For each scan two data storage cycles were employed. During the first, a reference video signal with the scanner head stationary in an unblemished area of the tube was stored. Then, the stepping motor was started and the digital signal from the moving scanner was subtracted from the stored reference signal. The difference was near zero for unblemished surface areas and increased due to the presence of defects which reduced the amount of reflected light.

Figure 4A:
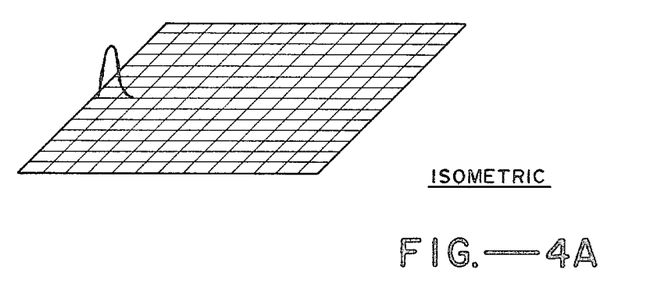
FIGS. 4A–4C illustrate three types of display formats (isometric, contour and profile) for the output image of a region of tube interior containing a simulated defect.
Figure 4B:
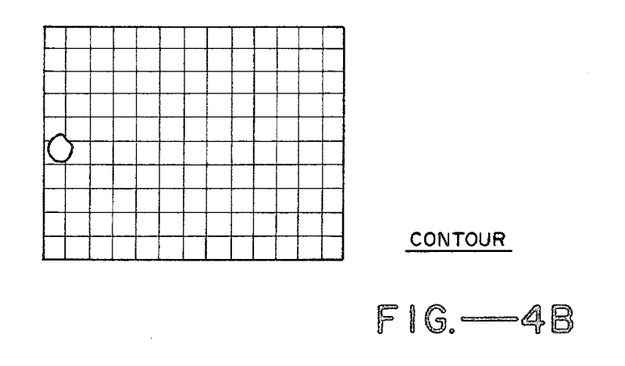
Figure 4C:
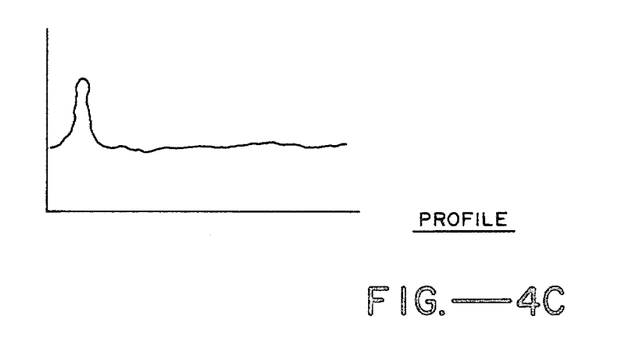

FIG. 4 illustrates the three types of display formats (isometric, contour and profile) obtained for a 0.050 inch diameter pit using the scanner arrangement of FIG. 1.

Figure 5:
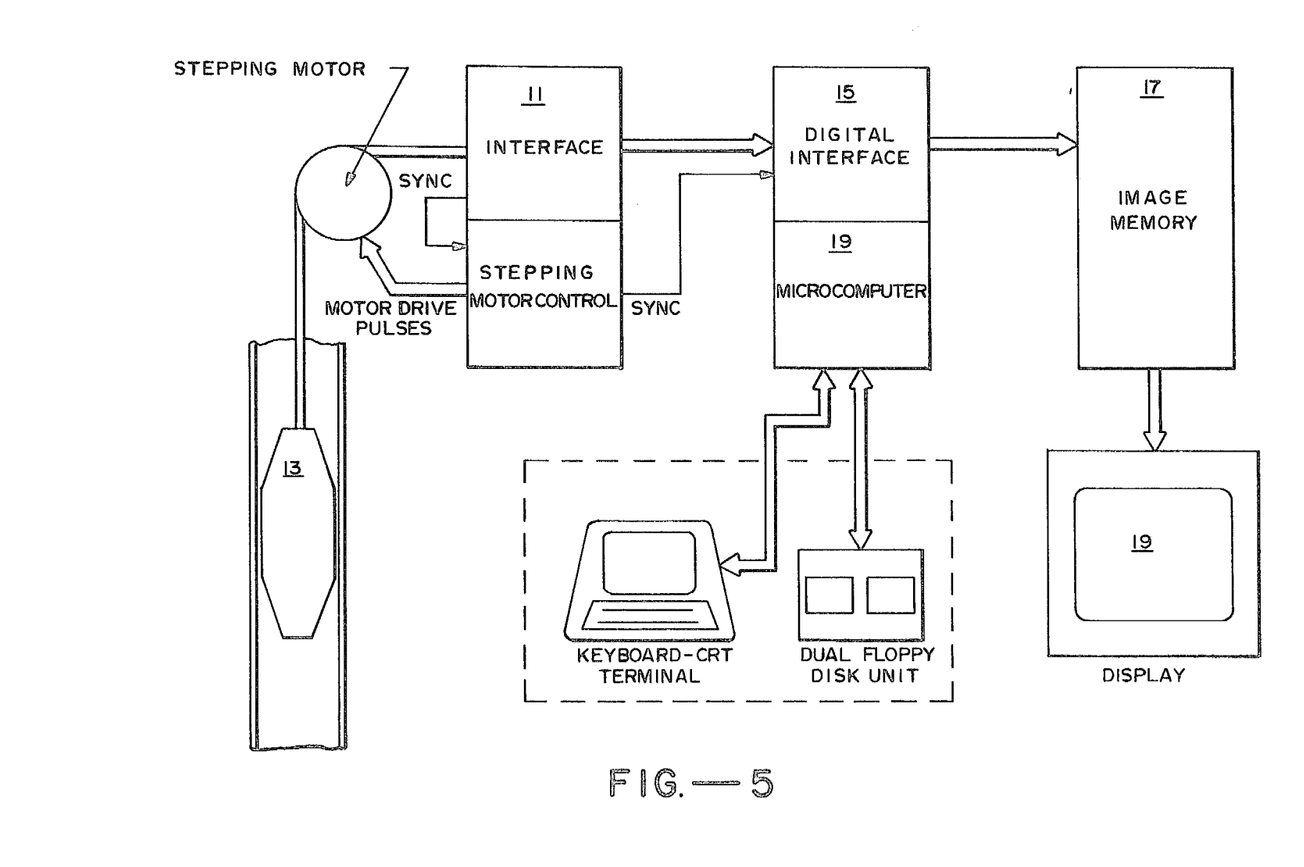
FIG. 5 is a functional block diagram of an alternative embodiment of an optical scanning system in accordance with the invention.

FIG. 5 is a functional block diagram of another embodiment of data acquisition and display system. In the camera interface 11 the video signal from the Reticon Array in scanner 13 is digitized and is compared to a stored reference signal in digital interface 15. The difference signal is stored in a Grinnell Model GMR-27 digital image memory 17. The contents of the memory are continuously displayed on a TV monitor 19. The motion of the scanner head is synchronized to the array readout by pulsing the stepping motor after an integral number of readout lines. In addition, the display is scrolled in synchronization with the scanner motion with the newest data appearing at the bottom or top of the picture depending on the scanner direction. When the scanner is stopped, the scrolling stops and the most recent picture is displayed continuously.

The method of generating the stored reference signal is selected by the operator from two alternatives: (1) the video signal from an unblemished area of the tube is simply stored, or (2) a running average of the most recent 256 lines is stored and updated continuously as new data arrives.

The data storage and display scrolling is controlled by a microcomputer 19 such as a PDP 11/03 LC. The computer can also be used for digital readout of image memory on terminal 21 to provide quantitative information on defects. In addition to the TV display, the video information from the memory may be recorded using a video tape recorder.

Figure 6A:
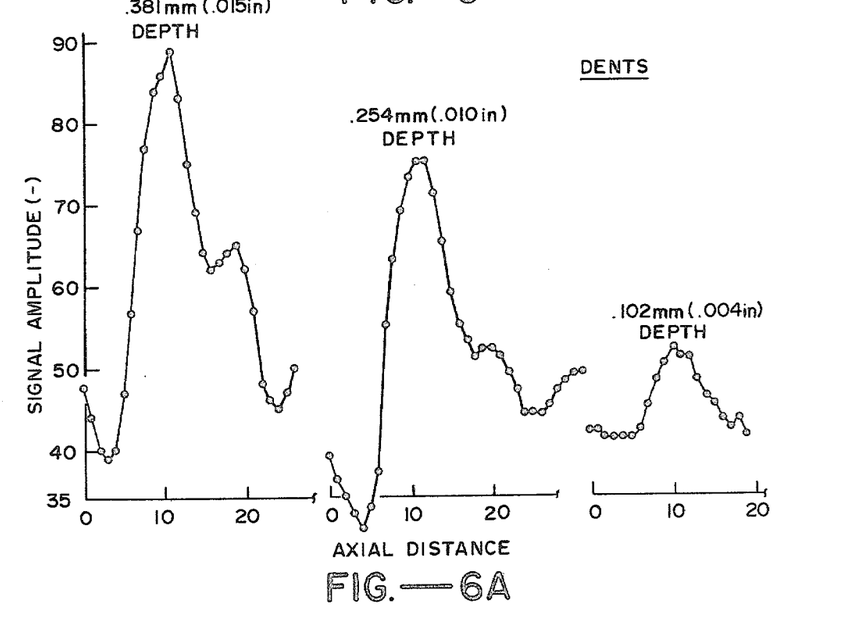
FIGS. 6A–6E are plots of signal amplitude versus distance in a tube indicating the signal response for dents, holes, pits, and cracks.
Figure 6B:
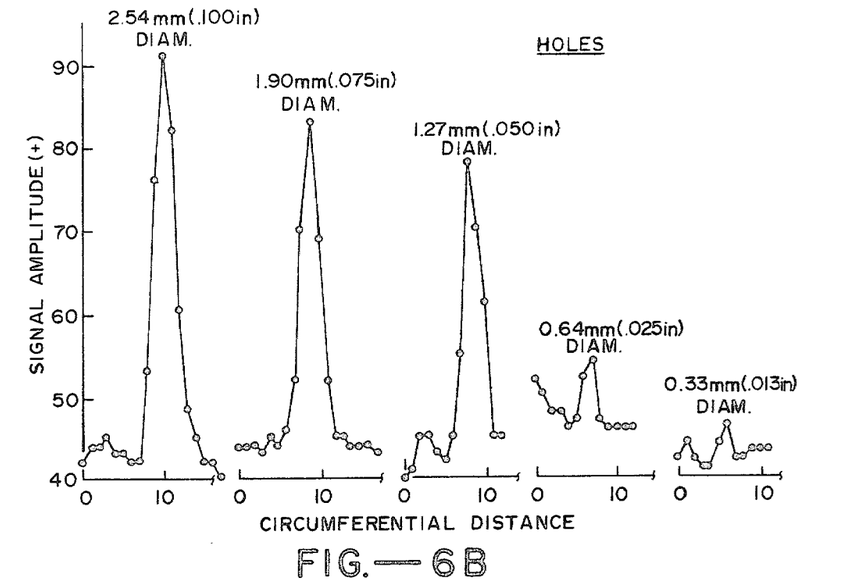

FIGS. 6A-6E are plots of signal readouts for dents, holes, pits, and cracks, respectively, in test samples using the apparatus described hereinabove. FIG. 6A shows the signal amplitude for dents of 0.381 mm, 0.254 mm, and 0.102 mm depths along an axial distance as indicated. FIG. 6B shows signal amplitude for holes of 2.54 mm, 1.90 mm, 1.27 mm, 0.64 mm, 0.33 mm diameter along circumferential distance.

Figure 6C:
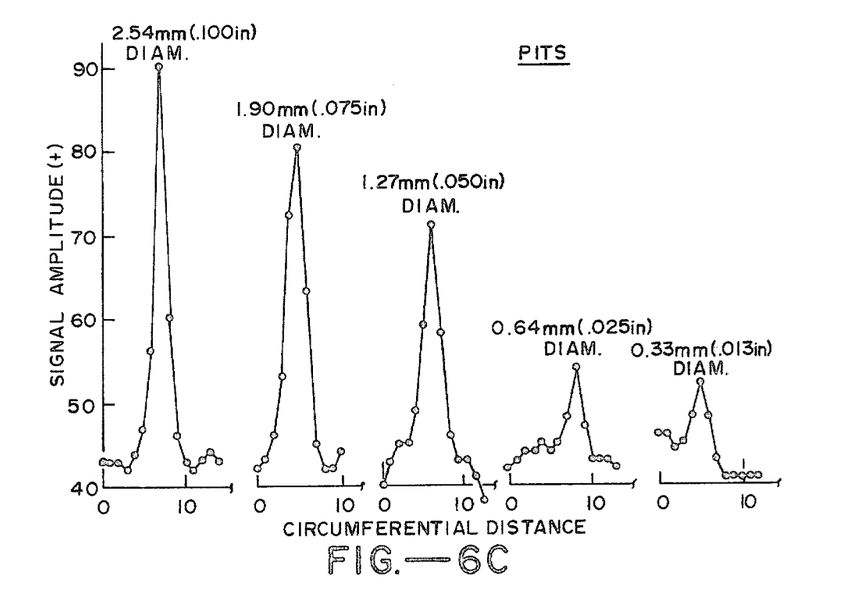
Figure 6D:
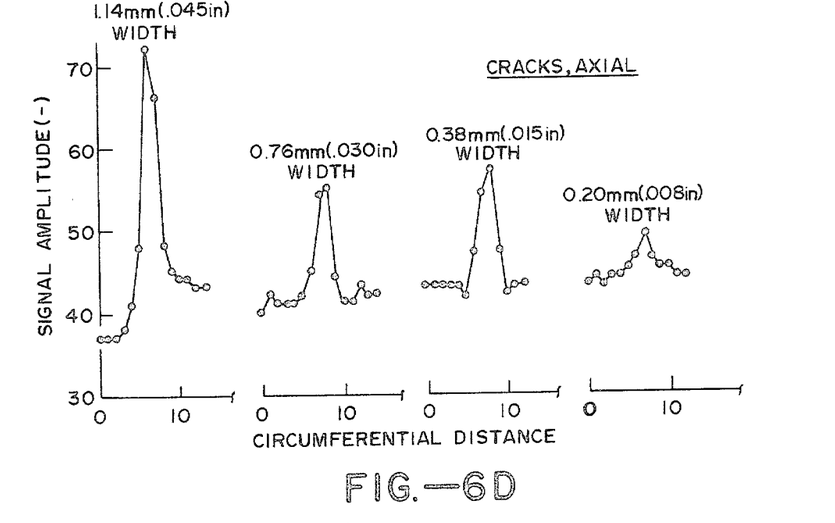
Figure 6E:
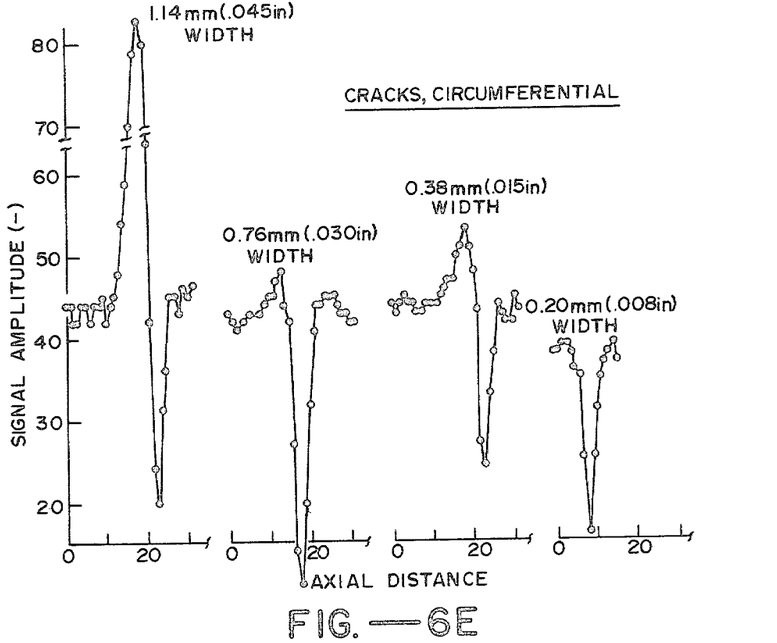

FIG. 6C shows signal amplitude for pits having diameters of 2.54 mm, 1.90 mm, 12.7 mm, 0.64 mm, and 0.33 mm spaced along circumferential distance as indicated. FIG. 6D is signal amplitude for axial cracks having widths of 1.14 mm, 0.36 mm, 0.38 mm, and 0.20 mm along circumferential distance as indicated. FIG. 5E is signal amplitude for circumferential cracks of 1.14 mm, 0.76 mm, 0.38 mm, and 0.20 mm along axial distance as indicated.

Figure 7A:
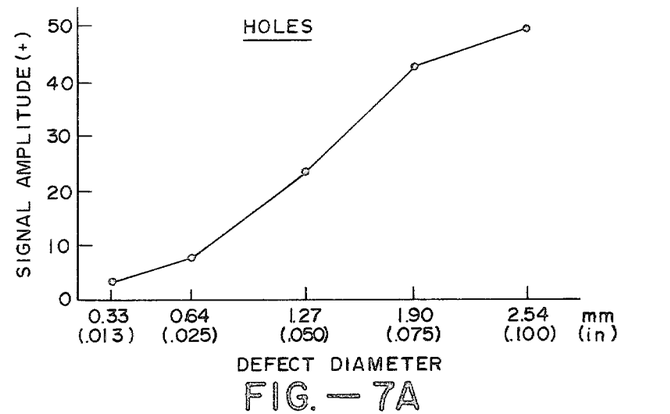
FIGS. 7A–7E are plots of signal amplitude versus defect dimensions for dents, holes, pits and cracks.
Figure 7B:
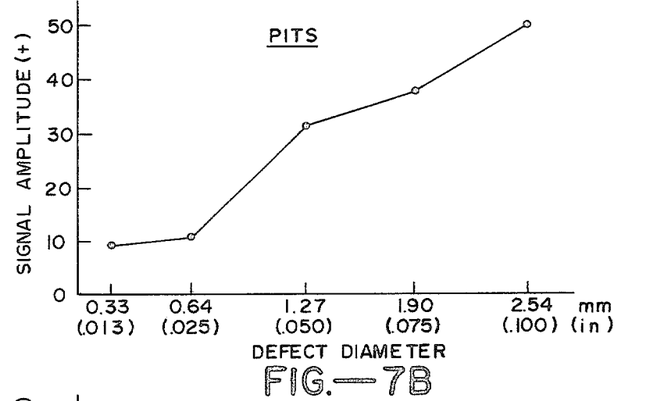
Figure 7C:
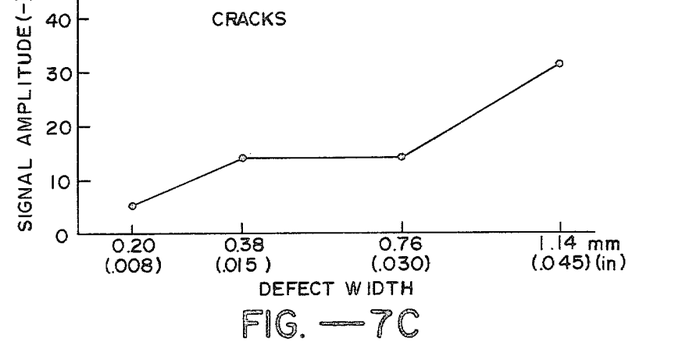
Figure 7D:
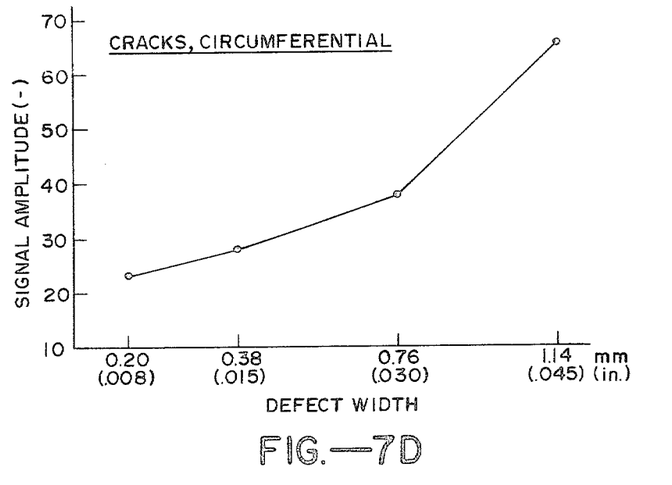
Figure 7E:
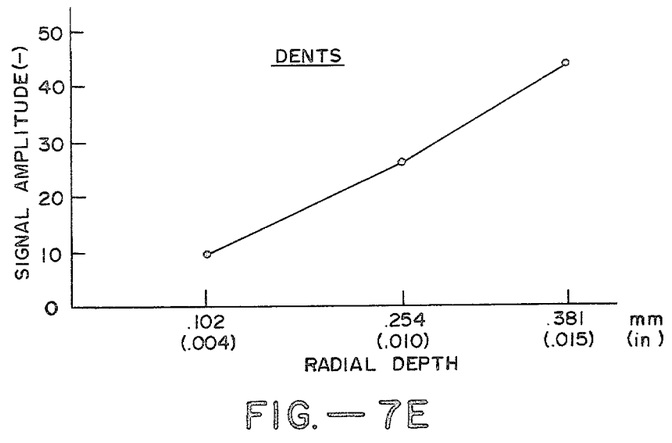

FIGS. 7A-7E are plots of signal amplitude versus defect dimensions. In FIG. 7A the signal amplitude is plotted versus defect diameter for holes. In FIG. 7B the signal amplitude is measured for defect diameter of pits. FIG. 7C is signal amplitude versus defect width for axial cracks, and FIG. 7D is signal amplitude versus defect width for circumferential cracks. FIG. 7E is a plot of signal amplitude versus radial depth for dents.

The method and apparatus for optically scanning the interior surface of a pipe in accordance with the present invention has proved to be more accurate and reliable than any current techniques heretofore employed. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. Means for inspecting and imaging the interior surface of a tube and the like comprising a light source, photodiode array means for receiving light and generating an electrical signal in response thereto, means for directing light onto said means for receiving light, and carrier means for supporting and moving said light, said means for receiving light, and said means for directing light.

2. Means for inspecting as defined by claim 1 wherein said means for directing light comprises a lens for focusing light onto said means for receiving light and mirror means for reflecting light to said lens.

3. Means for inspecting as defined by claim 2 wherein said mirror means comprises a convex mirror for receiving light reflected from said interior surface and a flat mirror for receiving light from said convex mirror.

4. Means for inspecting as defined by claim 3 wherein said carrier means includes an elongated body with a cavity defined therein, said means for receiving light and generating an electrical signal being mounted in said cavity, said light source being mounted to said carrier to illuminate said interior surface, said elongated body having optical window means with said convex mirror mounted within said optical window means for receiving light reflected from said interior surface, and said flat mirror being mounted at one end of said cavity for receiving reflected light from said convex mirror and directing said light to said lens.

5. Means for inspecting as defined by claim 4 wherein said carrier includes a plurality of wheels for engaging said interior surface and moving said carrier along said interior surface.

6. The method of inspecting for defects in the interior surface of a tube and the like comprising the steps of
(a) illuminating the interior surface of said tube,
(b) directing reflected light from said interior surface to an array of photodiodes, and
(c) generating from said photodiode array a plurality of electrical signals proportional to the intensity of reflected light.

7. The method as defined by claim 6 and further including the steps of
(d) converting said electrical signal to a digital signal,
(e) storing a digital reference signal for an unblemished area of said interior surface, and
(f) subtracting said converted electrical signal from said stored reference signal to produce a difference signal.

8. The method as defined by claim 7 and further including the steps of
(g) storing said difference signal in a digital image memory the contents of which are continuously displayed on a video monitor to produce an image of the interior surface of the tube, and
(h) scrolling the display so that the picture moves in synchronism with the scanner head.

* * * * *